United States Patent
Liu et al.

(10) Patent No.: US 9,970,857 B2
(45) Date of Patent: May 15, 2018

(54) AUTOMATIC COMPENSATION METHOD, DEVICE, AND CORRESPONDING FLOW CYTOMETER

(71) Applicants: SHENZHEN MINDRAY BIO-MEDICAL ELECTRONICS CO., LTD., Shenzhen (CN); BEIJING SHEN MINDRAY MEDICAL ELECTRONICS TECHNOLOGY RESEARCH INSTITUTE CO., LTD., Beijing (CN)

(72) Inventors: Penghao Liu, Shenzhen (CN); Wenheng Guo, Beijing (CN); Youlin Liu, Beijing (CN); Jian Jin, Beijing (CN); Huawen Yan, Beijing (CN); Lifang Dong, Beijing (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 44 days.

(21) Appl. No.: 15/289,826

(22) Filed: Oct. 10, 2016

(65) Prior Publication Data

US 2017/0097296 A1    Apr. 6, 2017

Related U.S. Application Data

(63) Continuation of application No. PCT/CN2014/075109, filed on Apr. 10, 2014.

(51) Int. Cl.
*G01N 15/14* (2006.01)
*G01N 33/483* (2006.01)
*G06F 19/26* (2011.01)

(52) U.S. Cl.
CPC ..... *G01N 15/1429* (2013.01); *G01N 33/4833* (2013.01); *G06F 19/26* (2013.01)

(58) Field of Classification Search
CPC .................................................. G01N 15/1429
(Continued)

(56) References Cited

U.S. PATENT DOCUMENTS

| 2004/0119974 | A1  | 6/2004 | Bishop et al. |
| 2005/0073686 | A1* | 4/2005 | Roth .................. G01N 15/1404 356/436 |

(Continued)

FOREIGN PATENT DOCUMENTS

| CN | 102177427 A   | 9/2011 |
| CN | 103180858 A   | 6/2013 |
| WO | 2007010236 A1 | 1/2007 |

OTHER PUBLICATIONS

Chen et al., AnnexinVPI Detection of Cell Apoptosis by Flow Cytometry to Determine the Positive Boundary Value and Compensation Value, J Mod Lab Med., Jul. 31, 2008, vol. 23, No. 4.

(Continued)

*Primary Examiner* — Roy M Punnoose
(74) *Attorney, Agent, or Firm* — Kory D. Christensen; Polsinelli LLP

(57) ABSTRACT

This disclosure provides automatic compensation methods, corresponding devices and a corresponding flow cytometer. The automatic compensation method includes: determining a base cell population and a reference cell population in the cell populations according to positions of the cell populations in a dot plot that needs to be compensated, where the base cell population is a double negative cell population and the reference cell population is a single positive cell population adjacent to the base cell population in a compensating direction (S10); calculating automatically a compensation value through a progressive approximation algorithm according to a position of the base cell population, and updating the dot plot with the compensation value, so that the position difference between the reference cell population (Continued)

and the base cell population both in the dot plot in the compensating direction is within a predetermined range (S16).

20 Claims, 9 Drawing Sheets

(58) Field of Classification Search
USPC .......................................................... 356/338
See application file for complete search history.

(56) References Cited

U.S. PATENT DOCUMENTS

| 2008/0194508 A1 | 8/2008 | Christensen et al. |
| 2014/0220621 A1* | 8/2014 | Durack .............. G01N 15/1427 435/34 |

OTHER PUBLICATIONS

Tao et al., Compensative Problem in Multi-Parameter Measurement of Flow Cytometry, Journal of Beijing Medical University, 1996, pp. 39-41, vol. 28, No. 1.

* cited by examiner

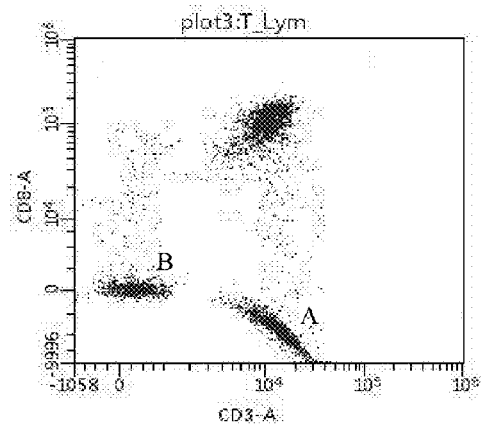
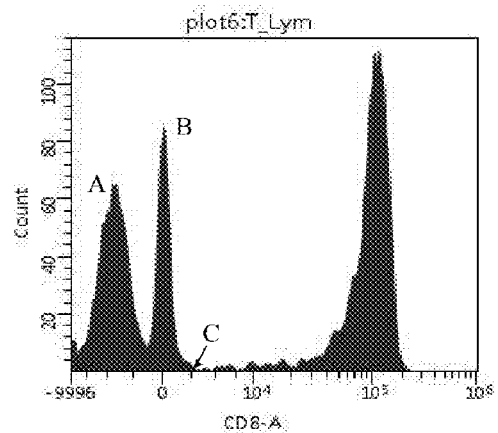
FIG. 8a          FIG. 8b
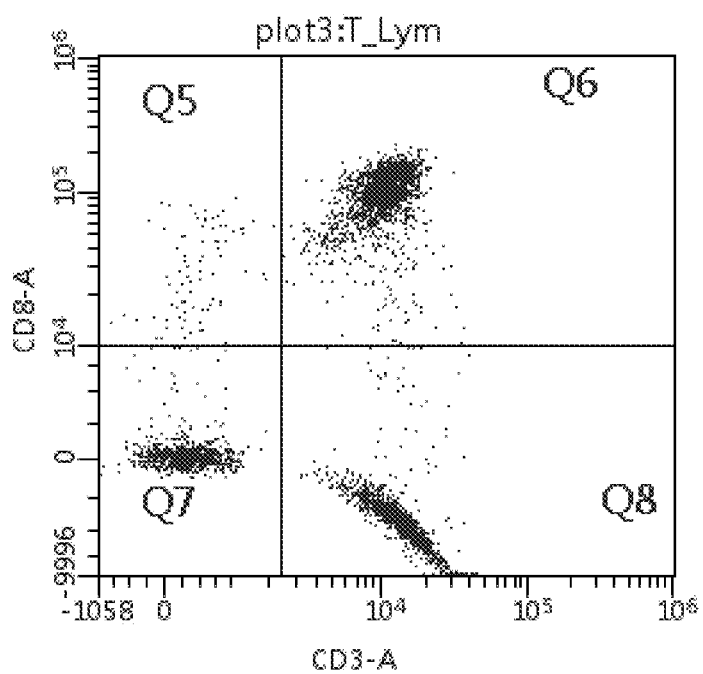
FIG. 9

AUTOMATIC COMPENSATION METHOD, DEVICE, AND CORRESPONDING FLOW CYTOMETER

TECHNICAL FIELD

The present disclosure relates to medical equipments, particularly to an automatic compensation method, device and corresponding flow cytometer.

BACKGROUND

Flow cytometer can receive photoelectric signals generated by irradiating cells with laser and graphically present the photoelectric signals for the analysis of the user. Scattered light signals and fluorescence signals of the photoelectric signals can represent physical and chemical properties of the cells, such as the size of the cell, the graininess and the expression of antigen molecules, etc.

FIG. 1 schematically shows an existing flow cytometer, which mainly includes an optical system, a fluid system, a mechanical system, a control and signal processing system, related peripherals and a software system (not shown). The fluid system is mainly used to form a sample stream with the sample to be analyzed and enable the flow of the sample stream to be adjustable. The optical system is mainly used to generate laser to irradiate the sample stream to generate forward and side fluorescence signals. The control and signal processing system is mainly used to perform photoelectric conversion and control the cytometer. The software system is mainly used to represent the information about the height, area or the like of particles in visual graphs by setting related photoelectric conversion parameters and pulse identification parameters, for the analysis of the user by a variety of tools.

Representing the information about the height, area or the like of the particles in visual graphs is generally implemented by a routine as shown in FIG. 2. In this routine, the sample stream flows through a flow chamber, and the cells in the stream generate scattered light signals and fluorescence signals after being irradiated by the laser. The photoelectric conversion unit converts these optical signals into electric signals, and performs suitable processing on them. The processed signals are analog signals, which need to be converted into digital signals by AD conversion (analog to digital conversion) and AD acquisition for following data processing. Since the data the user needs is the information about the height, area or the like of the particles, pulse identification needs to be performed on the acquired digital signals in order to identify the effective particles to further calculate the height and area of the particles. Then, the information about the height or the area is transmitted to a computer and translated into graph such as dot plot, histogram or the like by the software system.

FIG. 3 schematically shows an electric signal converted from an optical signal of an existing flow cytometer, which undergoes the photoelectric conversion and circuit processing and is presented in voltage. A typical dot plot is shown in FIG. 4.

The fluorescence signals are excited by irradiating fluorescein with the laser. However, the wavelengths of the generated fluorescence signals are generally not a fixed wavelength as in an ideal state, but distributed in a certain distribution curve. In order to acquire the fluorescence data representing a certain property, the flow cytometer uses bandpass filters to filter out interference signals to ensure that most of the acquired signals are fluorescence signals which can represent the properties of the irradiated subject. FIG. 5 schematically shows the wavelength distribution and the working principle of the bandpass filter. As shown in FIG. 5, based on the currently used laser, fluorescein and bandpass filter, it can not be completely ensured that the signals from a variety of channels will not interfere with each other. In FIG. 5, the interference between two channels exists at A and B, which will lead to deviation of the data of the irradiated subject acquired in corresponding channels. In order to overcome this drawback, a fluorescence compensation method is generally used in the art to eliminate the interference between the channels, such that the data which can truly represent the actual properties of the irradiated subject can be shown in the presented graphs. The fluorescence compensation is generally implemented in the form of a table, where each table cell represents a correction in percentage to the leakage (interference) from a channel A to a channel B.

However, for the fluorescence compensation method by the table, it is needed to acquire the data of the plurality of fluorescence channels using a plurality of tests under a known voltage, and compensation values of the plurality of table cells need to be calculated according to the data of the plurality of channels, which is costly and time-consuming. Furthermore, in clinical practice, the compensation values of the graphs often need to be adjusted and the user usually tries to adjust the compensation values several times until particle clusters are distributed in the dot plot in a "smooth vertical and horizontal" shape, i.e., cell populations are substantially equally positioned in a certain direction. For example, a target dot plot shown in FIG. 6 may be obtained from the data of the dot plot shown in FIG. 4 by compensating the dot plot after a plurality of manual adjustments of the compensation system.

However, the inventors have found that there are some difficulties for the user to implement the graph-based compensation using the existing method. First, after the user determines a direction for compensation, it will take experience for the user to determine which cell of a compensation matrix needs to be adjusted, which can only be accurately determined with very rich experience. Second, when the user performs manual adjustment, a suitable compensation value can generally be obtained after a plurality of cycles of compensation adjustment, graph observation, and reviewing and analysis of statistical results, which is cumbersome, complicated and inaccurate.

SUMMARY

In order to eliminate the drawbacks of the existing technologies, the present disclosure provides an automatic compensation method, device and corresponding flow cytometer, by which the graphs can be automatically adjusted and compensated, thereby reducing user's workload and increasing compensation accuracy.

To solve the problems mentioned above, in an aspect, an embodiment of the present disclosure can provide an automatic compensation method for analyzing and processing flow data. The method may include the following steps:

determining a base cell population and a reference cell population in a plurality of cell populations according to positions of the plurality of cell populations in a dot plot which needs to be compensated, where the base cell population may be a double-negative cell population and the reference cell population may be a single-positive cell population adjacent to the base cell population in a compensating direction; and automatically calculating a compensation value through a progressive approximation algorithm according to based on a position of the base cell population and compensating particles of the plurality of cell populations in the dot plot with the compensation value such that a position difference between the reference cell population and the base cell population in a compensated direction in the compensated dot plot is within a predetermined range.

Preferably, determining the base cell population in the plurality of cell populations according to the positions of the plurality of cell populations in the dot plot which needs to be compensated may include:

compensating the plurality of cell populations in the dot plot with a first compensation value, where the first compensation value may be an overcompensation value; and projecting the plurality of cell populations onto the compensating direction and the compensated direction respectively to obtain histograms and determining one of the plurality of cell populations as the base cell population according to graphical peak features of the histograms.

Preferably, determining the base cell population in the plurality of cell populations according to the positions of the plurality of cell populations in the dot plot which needs to be compensated may include:

acquiring a cell population contour using an image algorithm at a lower-left region of the dot plot and determining a cell population corresponding to the cell population contour as the base cell population.

Preferably, after determining the base cell population and the reference cell population in the plurality of cell populations, the method may further include:

dividing the dot plot into four regions according to the position of the base cell population such that the base cell population is located in a lower-left region.

Preferably, automatically calculating the compensation value through the progressive approximation algorithm according to the position of the base cell population and compensating the particles of the plurality of cell populations in the dot plot with the compensation value may include:

compensating the particles of the plurality of cell populations in the dot plot with the compensation value using the following formula:

a compensation resulting value of each particle in the compensated direction=a current measurement value of each particle in the compensated direction−the compensation value*a current measurement value of each particle in the compensating direction;

where a compensation resulting value of each particle in the compensating direction may remain unchanged relative to its current measurement value in the compensating direction.

Preferably, the method may further include calculating a coarse adjustment compensation value and compensating the dot plot with the coarse adjustment compensation value, where the coarse adjustment compensation value may be calculated using the following formula:

(a measurement value of the reference cell population in the compensated direction−a measurement value of the base cell population in the compensated direction)/a measurement value of the reference cell population in the compensating direction.

Preferably, the progressive approximation algorithm may be an iterative algorithm, and automatically calculating the compensation value through the progressive approximation algorithm according to the position of the base cell population and compensating the particles of the plurality of cell populations in the dot plot with the compensation value may include:

setting the coarse adjustment compensation value as an initial compensation value or setting an initial compensation value, and setting an adjustment step length and an iteration termination condition; and compensating the plurality of cell populations in the dot plot and determining whether the compensated reference cell population meets the iteration termination condition; and if no, automatically adding or subtracting the initial compensation value by the adjustment step length to obtain a current compensation value, and continuing to compensate the plurality of cell populations in the dot plot, until the iteration termination condition is met.

Preferably, the iteration termination condition may be:

an absolute value of a difference value between a median of the compensation resulting values of the base cell population in the compensated direction and a median of the compensation resulting values of the reference cell population in the compensated direction is less than a first predetermined value; or a ratio of an absolute value of a difference value between a median of the compensation resulting values of the base cell population in the compensated direction and a median of the compensation resulting values of the reference cell population in the compensated direction to the median of the compensation resulting values of the base cell population in the compensated direction or the median of the compensation resulting values of the reference cell population in the compensated direction is less than a second predetermined value; or an absolute value of a difference value between an average of the compensation resulting values of the base cell population in the compensated direction and an average of the compensation resulting values of the reference cell population in the compensated direction is less than a third predetermined value; or a ratio of an absolute value of a difference value between an average of the compensation resulting values of the base cell population in the compensated direction and an average of the compensation resulting values of the reference cell population in the compensated direction to the average of the compensation resulting values of the base cell population in the compensated direction or the average of the compensation resulting values of the reference cell population in the compensated direction is less than a fourth predetermined value.

Preferably, automatically adding or subtracting the initial compensation value by the adjustment step length to obtain the current compensation value and compensating the plurality of cell populations in the dot plot until the iteration termination condition is met may further include:

determining whether there is a reversion in magnitude between the median/average of the compensation resulting values of the particles of the base cell population in the compensated direction and the median/average of the compensation resulting values of the particles of the reference cell population in the compensated direction; and if yes, reducing the adjustment step length by a predetermined value and continuing the iteration.

Preferably, the progressive approximation algorithm may be a binary search algorithm.

Preferably, dividing the dot plot into four regions according to the position of the base cell population may include:

dividing the dot plot into four regions by generating a quadrant gate in the dot plot, where the quadrant gate may be a regular quadrant gate which is formed by one straight line in a horizontal direction and one straight line in a vertical direction, or an irregular quadrant gate which is formed by at least one lines in a horizontal direction and at least one lines in a vertical direction.

Preferably, the method may further include:

before the automatic compensation, determining at least one expected target compensating directions of the plurality of cell populations in the dot plot and displaying the target compensating directions in graph form for user's selection.

Preferably, the method may further include:

before or after the automatic compensation, manually adjusting the compensation value and compensating the plurality of cell populations in the dot plot with the adjusted compensation value.

Correspondingly, in another aspect, an embodiment of the present disclosure provides an automatic compensation device for analyzing and processing flow data. The device may include:

a base cell population determination unit which may be used to determine a base cell population and a reference cell population in a plurality of cell populations according to positions of the plurality of cell populations in a dot plot which needs to be compensated, where the base cell population may be a double-negative cell population and the reference cell population may be a single-positive cell population adjacent to the base cell population in a compensating direction; and a compensation unit which may be used to automatically calculate a compensation value through a progressive approximation algorithm according to a position of the base cell population and update the dot plot with the compensation value such that a position difference between the reference cell population and the base cell population in the dot plot in a compensated direction is within a predetermined range.

Preferably, the base cell population determination unit may include:

an overcompensation subunit which may be used to compensate the plurality of cell populations in the dot plot with a first compensation value, where the first compensation value may be an overcompensation value; and a projection subunit which may be used to project the plurality of cell populations onto the compensating direction and the compensated direction respectively to obtain histograms and determine one of the plurality of cell populations as the base cell population according to graphical peak features of the histograms.

Preferably, the base cell population determination unit may include:

a contour determination subunit which may be used to acquire a cell population contour using an image algorithm at a lower-left region of the dot plot and determine a cell population corresponding to the cell population contour as the base cell population.

Preferably, the device may further include:

a region division unit which may divide the dot plot into four regions according to the position of the base cell population such that the base cell population is located in a lower-left region.

Preferably, the compensation unit may further include:

a compensation subunit which may be used to compensate particles of all of the plurality of cell populations in the dot plot with the compensation value using a following formula:

a compensation resulting value of each particle in the compensated direction=a current measurement value of each particle in the compensated direction−the compensation value*a current measurement value of each particle in the compensating direction;

where a compensation resulting value of each particle in the compensating direction may remain unchanged relative to its current measurement value in the compensating direction.

Preferably, the device may further include a coarse adjustment compensation value calculation subunit which may be used to calculate a coarse adjustment compensation value with a following formula:

the coarse adjustment compensation value=(a measurement value of the reference cell population in the compensated direction−a measurement value of the base cell population in the compensated direction)/a measurement value of the reference cell population in the compensating direction.

Preferably, the progressive approximation algorithm used by the compensation unit may be an iteration algorithm, and the compensation unit may further include:

a setting subunit which may be used to set the coarse adjustment compensation value as an initial compensation value or set an initial compensation value, and set an adjustment step length and an iteration termination condition; and an iteration subunit which may compensate the plurality of cell populations in the dot plot and determine whether the compensated reference cell population meets the iteration termination condition; and if not, the iteration subunit may automatically add the adjustment step length to or subtract the adjustment step length from the initial compensation value to obtain a current compensation value, and continue to compensate the plurality of cell populations in the dot plot with the current compensation value, until the iteration termination condition is met.

Preferably, the iteration termination condition may be:

an absolute value of a difference value between a median of the compensation resulting values of the particles of the base cell population in the compensated direction and a median of the compensation resulting values of the particles of the reference cell population in the compensated direction is less than a first predetermined value; or a ratio of an absolute value of a difference value between a median of the compensation resulting values of the particles of the base cell population in the compensated direction and a median of the compensation resulting values of the particles of the reference cell population in the compensated direction to the median of the compensation resulting values of the particles of the base cell population in the compensated direction or the median of the compensation resulting values of the particles of the reference cell population in the compensated direction is less than a second predetermined value; or an absolute value of a difference value between an average of the compensation resulting values of the particles of the base cell population in the compensated direction and an average of the compensation resulting values of the particles of the reference cell population in the compensated direction is less than a third predetermined value; or a ratio of an absolute value of a difference value between an average of the compensation resulting values of the particles of the base cell population in the compensated direction and an average of the compensation resulting values of the particles of the reference cell population in the compensated direction to the average of the compensation resulting values of the particles of the base cell population in the compensated direction or the average of the compensation resulting values of the particles of the reference cell population in the compensated direction is less than a fourth predetermined value.

Preferably, the iteration subunit may further include:

an adjustment step length updating subunit which may be used to determine whether there is a reversion between the median/average of the compensation resulting values of the base cell population in the compensated direction and the median/average of the compensation resulting values of the particles of the reference cell population in the compensated direction; and if yes, the adjustment step length updating subunit may reduce the adjustment step length by a predetermined value and the iteration subunit may then continue the iteration.

Preferably, the progressive approximation algorithm may be a binary search algorithm.

Preferably, the region division unit may divide the dot plot into four regions by generating a quadrant gate in the dot plot, where the quadrant gate may be a regular quadrant gate which is formed by one straight line in a horizontal direction and one straight line in a vertical direction, or an irregular quadrant gate which is formed by at least one lines in a horizontal direction and at least one lines in a vertical direction.

Preferably, the device may further include:

a target compensating direction determination unit which may be used to, before the automatic compensation, determine at least one expected target compensating directions of the plurality of cell populations in the dot plot and display the target compensating direction in graph form for user's selection.

Preferably, the device may further include:

a compensation value setting unit which may be used to manually adjust the compensation value and compensate the cell populations in the regions of the dot plot with the adjusted compensation value.

Correspondingly, in yet another aspect, an embodiment of the present disclosure also provides a flow cytometer which may include the automatic compensation device as described above.

The advantages of the embodiments of the present disclosure may be as follows.

The automatic compensation method, device and corresponding flow cytometer provided by the embodiments of the present disclosure can automatically form the quadrant gate according to the features and the position information of the respective cell populations in the dot plot, automatically perform the coarse adjustment compensation, and perform fine adjustment compensation using the progressive approximation algorithm. Therefore, a suitable compensation value can be automatically calculated and the dot plot can be automatically updated, such that the plurality of cell populations in the compensated dot plot are distributed in a smooth horizontal and vertical form.

The embodiments of the present disclosure enable automatic compensation using the graph-based adjustment. Therefore, user's workload is reduced and the accuracy is increased. Furthermore, since the compensation cell which needs to be compensated can be automatically set, the experience requirement for the user is greatly reduced.

BRIEF DESCRIPTION OF THE DRAWINGS

In order to describe the technical solutions of the present disclosure or the prior art more clearly, the drawings used in the description of the embodiments or the prior art will be described briefly below. Obviously, the drawings described below are only some embodiments of the present disclosure. For a person ordinarily skilled in the art, other drawings can be obtained based on these drawings without creative work.

FIG. 8a schematically shows a dot plot of an embodiment of an automatic compensation method provided by the present disclosure;

FIG. 8b schematically shows a histogram obtained by projecting onto a Y axis in FIG. 8a;

FIG. 9 schematically shows a dot plot in which a quadrant gate has been automatically generated in an embodiment of an automatic compensation method provided by the present disclosure;

DETAILED DESCRIPTION

Figure 1:
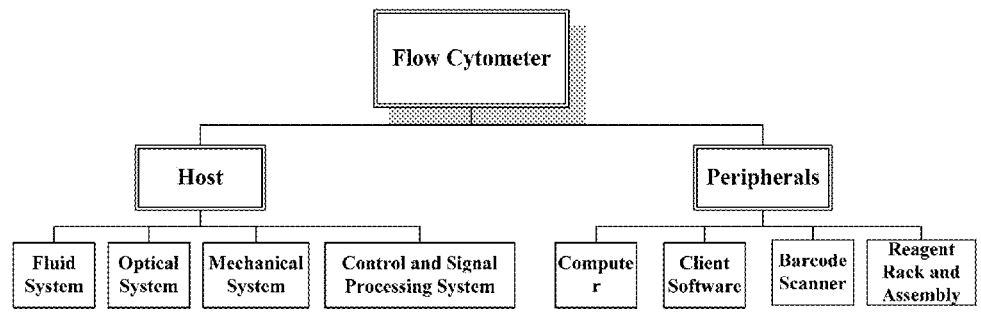
FIG. 1 schematically shows an existing flow cytometer.
Figure 2:
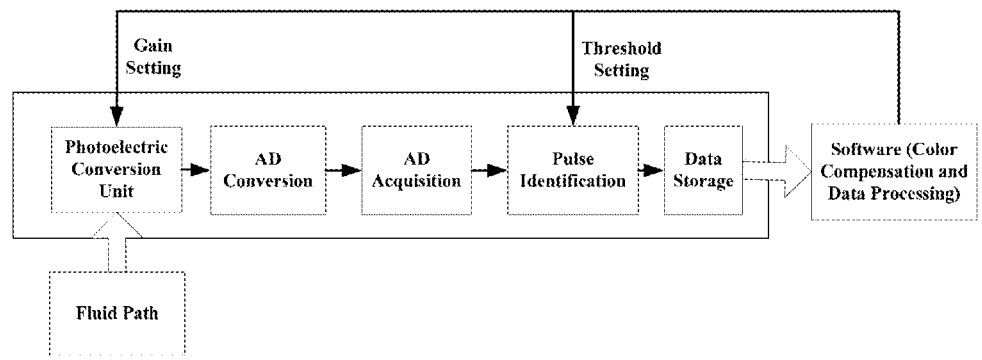
FIG. 2 schematically shows working principle of an existing flow cytometer.
Figure 3:
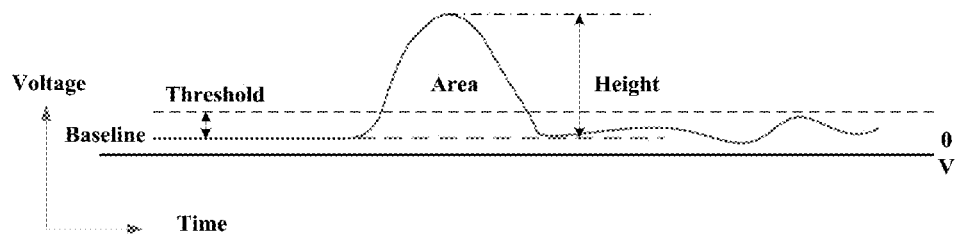
FIG. 3 schematically shows a waveform of an electric signal converted from an optical signal of an existing flow cytometer.
Figure 4:
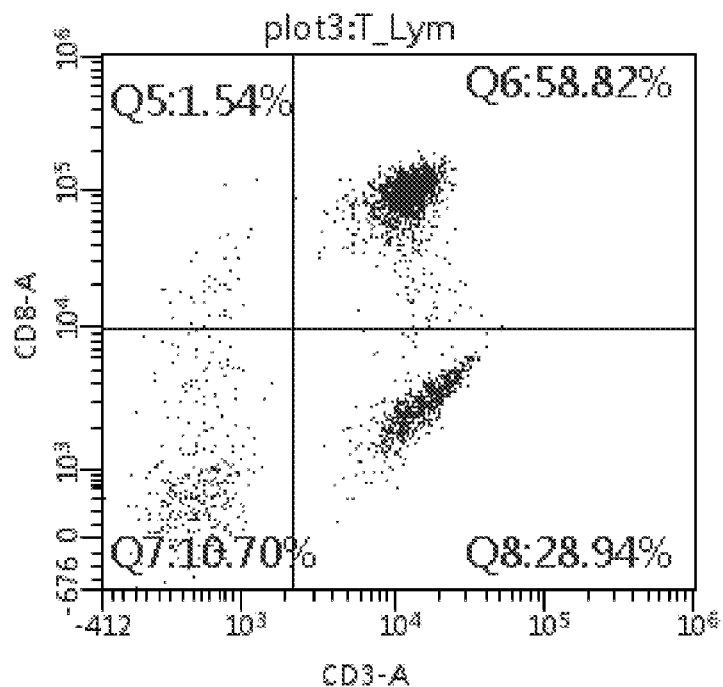
FIG. 4 is a typical dot plot displayed by an existing flow cytometer.
Figure 5:
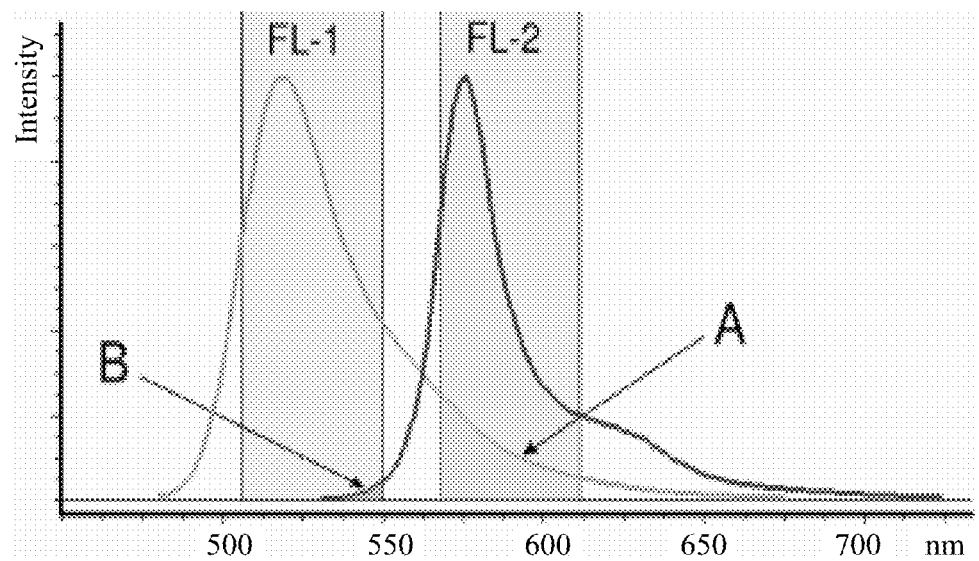
FIG. 5 schematically shows waveforms of fluorescence signals acquired by an existing flow cytometer using band-pass filters.
Figure 6:
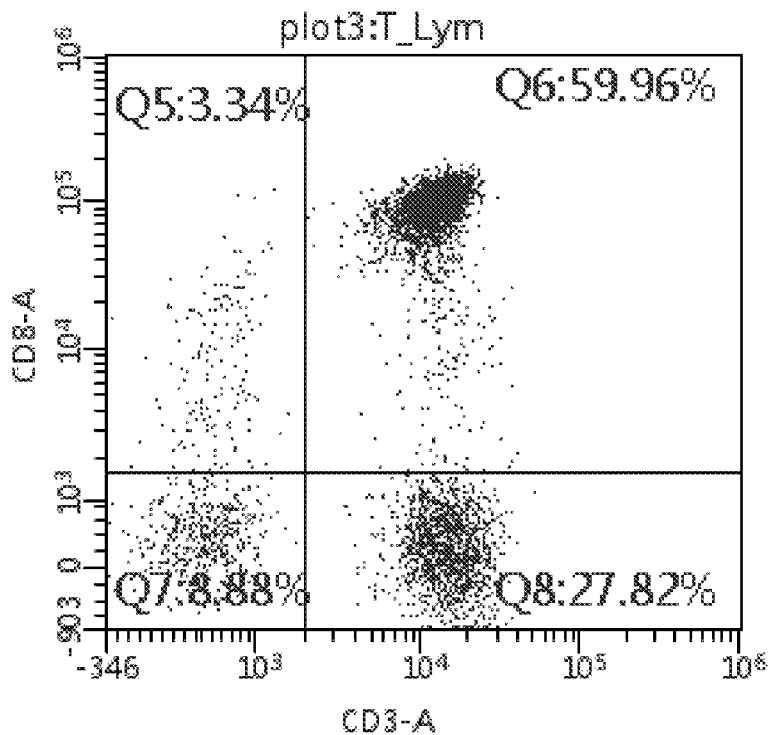
FIG. 6 shows an ideal dot plot of an existing flow cytometer after a manual adjustment.

The technical solutions of various embodiments of the present disclosure will be clearly and completely described hereinafter with reference to the drawings. However, it will be obvious that the described embodiments are parts, but not all, of the embodiments of the present disclosure. All other embodiments obtained by a person ordinarily skilled in the art according to the embodiments of the present disclosure without creative works will fall within the scope of protection of the present disclosure.

The embodiments of the present disclosure will be described with reference to the drawings below.

For the convenience of the following description, some terms recited in the following description will be briefly described first.

Flow data may refer to those data obtained by, using a sheath flow cytometry, irradiating fluorescent dyes on an analyte with a laser and acquiring intensities of scatter lights in a plurality of angles and intensities of fluorescence excitation lights.

Dot plot may refer to a two-dimensional plot generated by a flow cytometer, where the dot plot may contain two-dimensional feature information of a plurality of particles. An X axis and a Y axis of the dot plot may respectively represent one property of each particle. For example, in a dot plot, the X axis may represent CD3 property of lymphocytes, and the Y axis may represent CD8 property of the lymphocytes.

Compensation may refer to adjusting the value of each particle in a dot plot in at least one coordinate axis directions using a compensation value (i.e., a compensation coefficient). For example, the value in one coordinate axis direction may be adjusted while the value in another coordinate axis direction may not be adjusted.

Cell population may refer to a group of particles which are distributed in a certain region of a dot plot and formed by a plurality of particles which have the same properties, such as double-negative cell population, single-positive cell population, double-positive cell population or the like.

Compensating direction may refer to a coordinate direction in which coordinate values of the particles need not to be adjusted during compensation.

Compensated direction may refer to a coordinate direction in which coordinate values of the particles need to be adjusted during compensation.

Base cell population may refer to a cell population which is located as a reference position in a dot plot.

Reference cell population may refer to the single-positive cell population adjacent to the base cell population in the compensating direction.

In an embodiment, the particles in a dot plot may be compensated using the following formula:

a compensation resulting value of each particle in the compensated direction=a current measurement value of each particle in the compensated direction−a compensation value*a current measurement value of each particle in the compensating direction.

It should be noted that, during each compensation, the particles of all the cell populations in the dot plot need to be compensated, i.e., both the base cell population and the reference cell population are compensated using the formula above during each compensation, such that the measurement value of each particle in the compensated direction is adjusted to obtain the compensation resulting value of each particle in the compensated direction while the measurement value of each particle in the compensating direction remains unchanged.

The concepts of the embodiments of the present disclosure may be as following.

Figure 10:
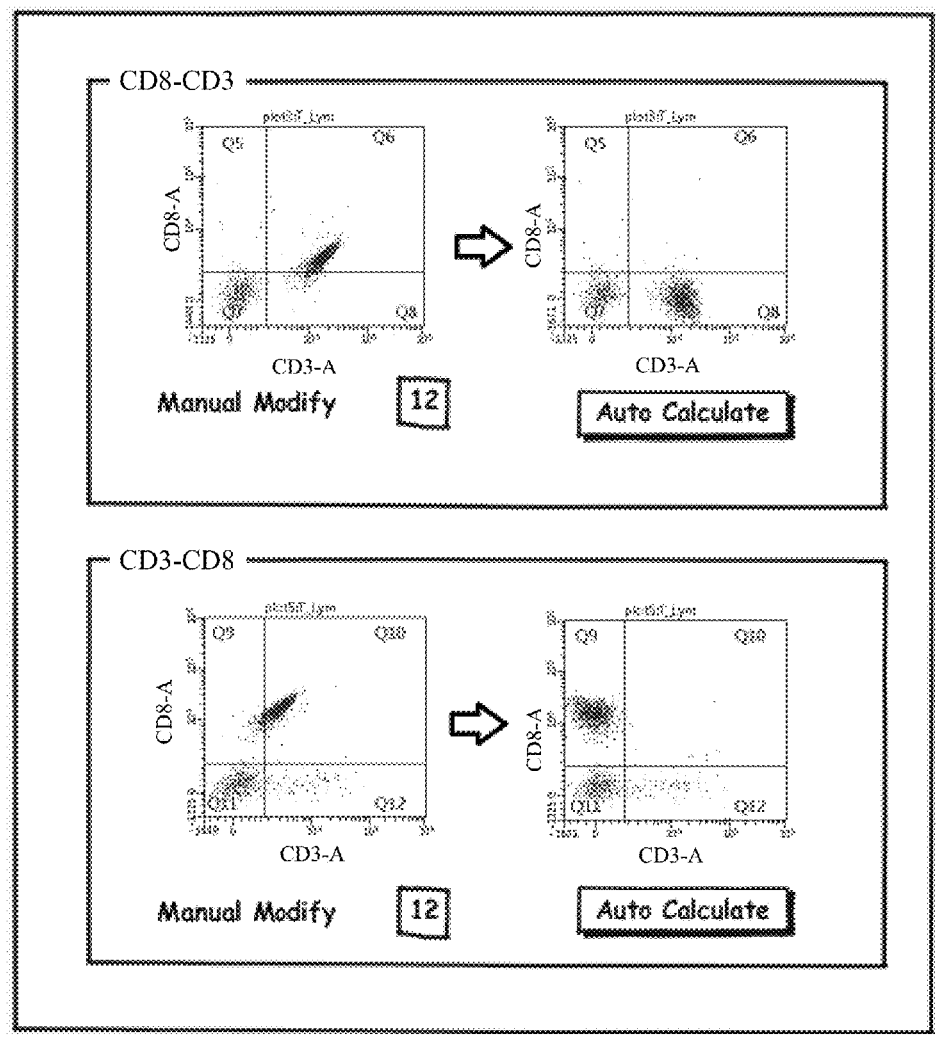
FIG. 10 schematically shows a compensating direction prompt interface of an embodiment of an automatic compensation method provided by the present disclosure.

When the flow data generated by a flow cytometer needs to be analyzed, a user may select, in an interaction interface, to perform compensation by manually adjusting the compensation values or by automatically calculating the compensation values using methods provided by the embodiments of the present disclosure. As shown in FIG. 10, a current dot plot and two desired compensating directions are shown in the interaction interface, and the user can determine one as the compensating direction under the graphical guidance. For example, in the case that the compensating direction in an upper location of FIG. 10 (i.e. a CD8-CD3 direction) is selected, the values of the particles in the dot plot in a CD8 direction will be compensated. In the case that the compensating direction in a lower location of FIG. 10 (i.e. a CD3-CD8 direction) is selected, the values of the particles in the dot plot in a CD3 direction will be compensated. It is understood that, in other embodiments of the present disclosure, each particle may also be compensated in two directions. That is, in an embodiment, the values of the particles in the dot plot are compensated in both the CD3 direction and the CD8 direction respectively. For convenience of description, the present disclosure will be described hereinafter with reference to the examples in which the particles in the dot plot are compensated using one direction as the compensating direction.

The user may also select to set the compensation value in a manual compensation box (which is a small box on a right side of "Manual Modify" in the figure). In FIG. 10, the current compensation value is 12, which can be manually adjusted by the user as needed. Or, the user may also select to automatically calculate the compensation value. When an "Auto Calculate" button is clicked in the figure, the methods provided by the embodiments of the present disclosure can automatically calculate a suitable compensation value according to graphic features of the current dot plot, and compensate the particles in the dot plot according to the calculated compensation value, thereby updating the dot plot. After the compensation value is automatically calculated and the particles are compensated, if the user considers that the compensation value automatically calculated is not suitable, the user can further manually adjust the compensation value. The principles and procedures of the automatic calculation of the compensation value of the embodiments of the present disclosure will be mainly described below.

Figure 7:
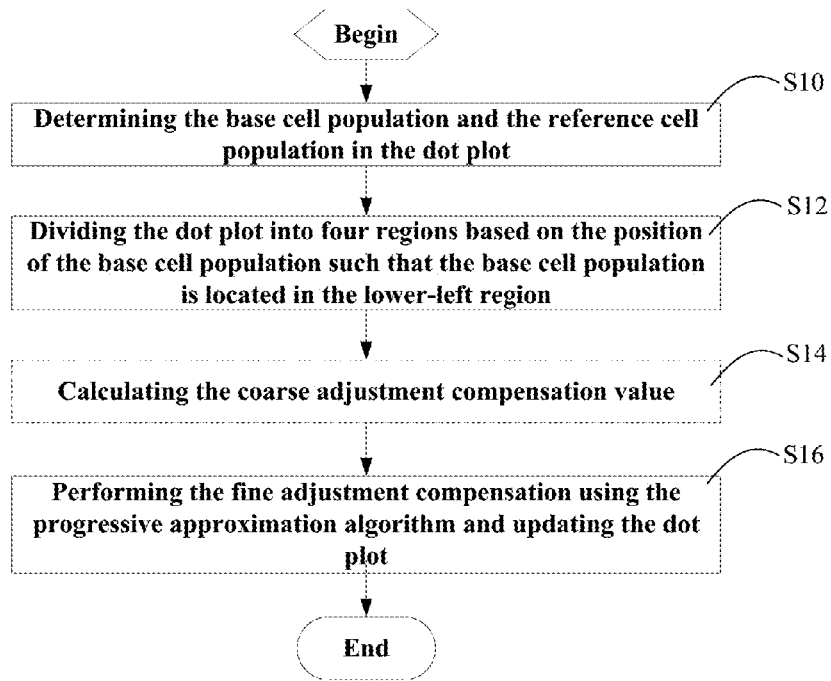
FIG. 7 is a flow chart of an embodiment of an automatic compensation method provided by the present disclosure.

FIG. 7 schematically shows a flow chart for an embodiment of an automatic compensation method provided by the present disclosure. In this embodiment, the method may include the following steps.

At step S10, a base cell population and a reference cell population in a plurality of cell populations may be determined according to positions of the plurality of cell populations in a dot plot which needs to be compensated. The base cell population may be a double-negative cell population. The reference cell population may be a single-positive cell population in a compensating direction. The dot plot may be generated by a flow cytometer.

At step S12, the dot plot may be divided into four regions according to a position of the base cell population, such that the base cell population can be located in a lower-left region.

At step S14, a coarse adjustment compensation value may be obtained. The step S14 may be optional.

At step S16, a compensation value may be automatically calculated through a progressive approximation algorithm according to the position of the base cell population, and the dot plot may be updated using the compensation value, such that a position difference between the reference cell population and the base cell population in the dot plot in a compensated direction is within a predetermined range. In the dot plot of this embodiment, the compensating direction may be perpendicular to the compensated direction.

The steps above will be described in details with reference to other drawings hereinafter.

The step S10 may further include the following steps.

The plurality of cell populations in the dot plot may be compensated using a first compensation value, where the first compensation value is an overcompensation value. The plurality of cell populations may be projected onto the compensating and compensated directions respectively to obtain histograms, and one cell population of the plurality of cell populations can be determined as the base cell population and the reference cell population can also be determined according to graphical peak features of the histograms.

This step may be on the basis of the following principles.

For example, in an embodiment, a double-negative cell population, a single-positive cell population and a double-positive cell population are contained in the dot plot shown in FIG. 8a. For the three cell populations, in the case that they are interfered by other channels, the position of the double-negative cell population in the dot plot is relatively stable and does not greatly deviate from its actual position, but the position of the single-positive cell population in the dot plot greatly deviates from its actual position. Therefore, the double-negative cell population may be determined as the base cell population, the direction of an X-axis (CD3) may be determined as the compensating direction, and a Y-axis (CD8) may be determined as the compensated direction.

First, the position of the base cell population (i.e. the double-negative cell population) in the dot plot may be determined.

In an embodiment of the present disclosure, the first compensation value may be set. The first compensation value may be a relatively large value, such as 50%. During the compensation of the dot plot, double-negative cells are not sensitive to the compensation value (i.e., the positions of the particles have not changed much by the compensation) while single-positive cells are very sensitive to the compensation value (i.e., the position change of the particles of the single-positive cell population after the compensation is larger than that of the particles of the double-negative cell population). Accordingly, a relatively large compensation value can separate the double-negative cell population and the single-positive cell population. After the dot plot is overcompensated by the first compensation value, the single-positive cell population may be adjusted to a negative region (marked as A in FIG. 8a) while the double-negative cells will be gathered nearby the coordinate origin (marked as B in FIG. 8a). It can be understood that, in order to observe the various cell populations in the dot plot more clearly, the coordinate values in the negative regions of the two coordinate axes (i.e. the compensating direction and the compensated direction) of the dot plot may be amplified in a double exponential manner, so as to clearly show the large amounts of negative data generated by the compensation.

Then, all of the particles in the dot plot may be projected onto the Y axis (i.e. the CD8 direction) to obtain a histogram. The histogram obtained by the projection may be as shown in FIG. 8b. It can be seen from FIG. 8b that two peaks exist at the coordinate origin and at the left side of the coordinate origin, which correspond to the double-negative cell population (B) and the overcompensated single-positive cell population (A), respectively. A first position may be determined on the right side of the peak at the coordinate origin, and the Y-axis coordinate value (i.e. the value in the CD8 direction) of the first position in the dot plot may be obtained. Specifically, in an example, the first position may be a position where the amount of the particles (the Count number) equals to a predetermined value (for example, "4") for the first time. For example, a first position C is shown in FIG. 8b. Similarly, all of the particles in the dot plot may be projected onto the X axis (i.e. the CD3 direction) to obtain another histogram (not shown), in which a single peak that corresponds to the double-negative cell population may exist near the coordinate origin. A second position may also be determined on the right side of the peak near the coordinate origin and the X-axis coordinate value (i.e. the value in the CD3 direction) of the second position in the dot plot may be obtained. Based on the Y-axis coordinate value and the X-axis coordinate value obtained above, a point may be determined in the dot plot as a center point of a quadrant gate, and the cell population located at a lower-left side of the center point may be the base cell population (the double-negative cell population).

In the step S12, according to the center point determined in the step S10, lines may be extended from the center point in a horizontal direction and a vertical direction, so as to form the quadrant gate in the dot plot. The quadrant gate may be comprised of lines in the horizontal direction and the vertical direction, and divide the dot plot into four regions (referring to the regions Q5, Q6, Q7 and Q8 shown in FIG. 9), such that the base cell population is located in a lower-left region (Q7) and the reference cell population is located (or partly located) in the region adjacent to the base cell population in the compensating direction (Q8). Specifically, in FIG. 9, the cell population located in the region Q7 may be the base cell population and the cell population located in the region Q8 may be the reference cell population.

It can be understood that, in other embodiments, the base cell population may be found and the quadrant gate may be formed in the steps S10 and S12 by other ways. For example, in an embodiment, a cell population contour may be obtained at the lower-left corner of the dot plot of FIG. 8a directly using an image algorithm (such as algorithms of dilation and erosion, etc.). The obtained cell population may be deemed as the base cell population. A point may be determined at the upper right of the edge of the base cells as the center point of the quadrant gate. According to the center point, lines may be extended in the horizontal direction and the vertical direction to form the quadrant gate in the dot plot. The quadrant gate may divide the dot plot into four regions such that the base cells are located in the lower-left region. In this way, a dot plot with a quadrant gate similar to FIG. 9 is also obtained.

Figure 12A:
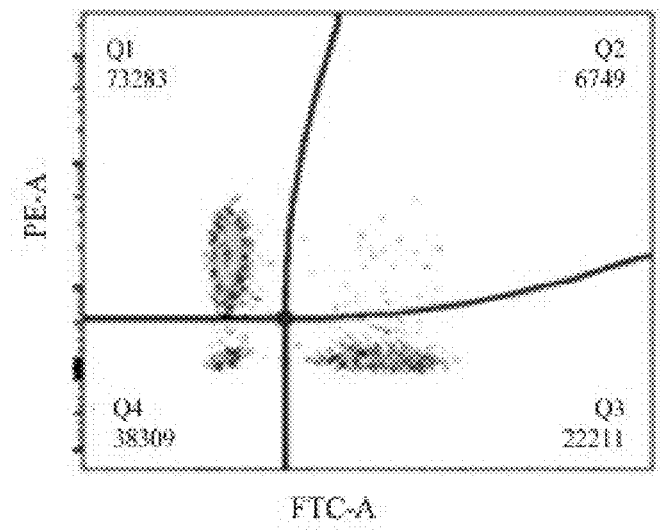
FIGS. 12a-12c schematically show dot plots in which quadrant gates have been automatically generated in other embodiments of an automatic compensation method provided by the present disclosure.
Figure 12B:
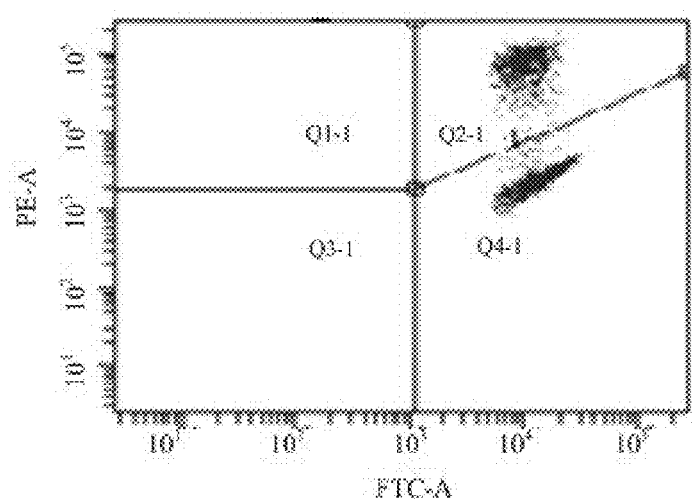
Figure 12C:
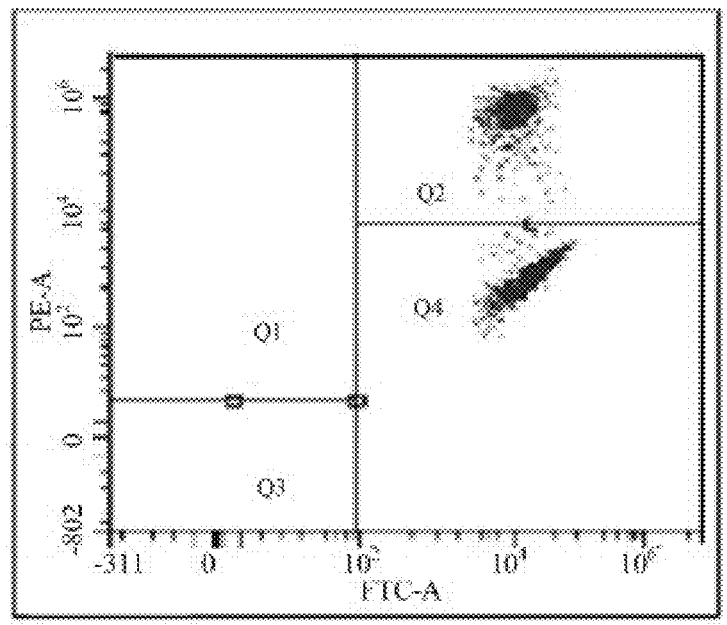

In FIG. 9, a regular quadrant gate (i.e. the line in the horizontal direction is perpendicular to the line in the vertical direction) is taken as an example of the quadrant gate. However, it can be understood that, in other embodiments, the quadrant gate may also be an irregular quadrant gate. For example, several irregular quadrant gates are shown in FIG. 12a to FIG. 12c. All of these irregular quadrant gates are required to divide the dot plot into four regions and to locate the base cell population in the lower-left region.

It can be understood that the measurement value of the base cell population or the reference cell population below is obtained by counting all particles in the region in which the base cell population or the reference cell population is located. That is, all particles in the lower-left region (such as the region Q7 in FIG. 9) are considered as the particles of the base cell population, and all particles in the region Q8 are considered as the particles of the reference cell population. The cell populations in other regions may be similarly counted.

At the step S14, t a coarse adjustment compensation value may further be calculated, and the dot plot may be compensated using the coarse adjustment compensation value.

The coarse adjustment compensation value may be calculated using the following formula:

a coarse adjustment compensation value=(a measurement value of the reference cell population in the compensated direction−a measurement value of the base cell population in the compensated direction)/a measurement value of the reference cell population in the compensating direction.

Specifically, the dot plot shown in FIG. 9 is taken as an example. The cell population in the region Q7 may be the base cell population, the cell population in the region Q8 may be the reference cell population, the X-axis direction (i.e. the CD3 direction) may be the compensating direction, and the Y-axis direction (i.e. the CD8 direction) may be the compensated direction.

The formula for calculating the coarse adjustment compensation value may be as following:

$$K_{12} = (Q8:O_{CD8} - Q7O_{CD8})/Q8:O_{CD3} \quad (5)$$

where $K_{12}$ is the coarse adjustment compensation value, $Q8:O_{CD8}$ is the measurement value(s) of the reference cell population located in the region Q8 in the CD8 direction (the compensated direction), $Q7:O_{CD8}$ is the measurement value(s) of the base cell population located in the region Q7 in the CD8 direction (the compensated direction), and $Q8:O_{CD3}$ is the measurement value(s) of the reference cell population located in the region Q8 in the CD3 direction (the compensating direction).

Specifically, the coarse adjustment compensation value may be obtained on the basis of the following principles.

Taking the dot plot in FIG. 9 as an example, the X-axis direction (i.e. the CD3 direction) is the compensating direction and the Y-axis direction (i.e. the CD8 direction) is the compensated direction. The compensation formula for each particles in the dot plot may be:

$$O_{CD8} = S_{CD8} + K_{12} * S_{CD3} \quad (1)$$

where $O_{CD8}$ is the measurement value in the CD8 direction (i.e. the Y-axis direction in FIG. 9), $S_{CD8}$ is an actual value in the CD8 direction (it is expected that a final compensation resulting value obtained by compensating the measurement value during the processing is close to the actual value), $S_{CD3}$ is an actual value in the CD3 direction, and $K_{12}$ is the coarse adjustment compensation value.

According to the formula (1), the following formula may be obtained:

$$S_{CD8} = O_{CD8} - K_{12} * S_{CD3} \quad (2)$$

For the base cell population located in the region Q8, the following formula may be obtained:

$$Q8:S_{CD8} = Q8:O_{CD8} - K_{12} * Q8:S_{CD3} \quad (3)$$

where Q8 represents the cell population located in the region Q8, and $Q8:S_{CD8}$ represents a set of actual values of the cell population located in the region Q8 in the CD8 direction.

Provided that the positions of the base cell population and the reference cell population in the dot plot are substantially at the same level after the compensation, the actual values of the reference cell population in the CD8 direction can be substantially the same with those of the base cell population in the CD8 direction. That is, $$Q8:S_{CD8} = Q7:S_{CD8},$$

which may be substituted into the formula (3) to obtain the following formula:

$$Q7:S_{CD8} = Q8:O_{CD8} K_{12} * Q8:S_{CD3} \quad (4)$$

The formula (4) may be rewritten as $$K_{12} = (Q8:O_{CD8} - Q7:S_{CD8})Q8:S_{CD3}$$

Since it is a coarse adjustment, it can be considered that $Q7:O_{CD8}$ approximately equals to $Q7:S_{CD8}$ and $Q8:O_{CD8}$ approximately equals to $Q8:S_{CD3}$. Therefore, the coarse adjustment compensation value $K_{12}$ may be obtained by:

$$K_{12} = (Q8:O_{CD8} - Q7:O_{CD8})/Q8:O_{CD3} \quad (5)$$

In the formula (5) above, the measurement values of the region Q7 and the region Q8 may be represented by medians. A median may refer to a numerical value of the particle in a middlemost position of a sequence, where the sequence is formed by sequencing all particles in one region according to their numerical values on the compensating direction and/or compensated direction. In this way, the interference of outlier(s) can be eliminated. All calculation items in the formula (5) above are measurable measurement values, and thus the coarse adjustment compensation value can be easily calculated.

It can be understood that, in other embodiments, the measurement values and the actual values of the region Q7 and the region Q8 in the formula (5) above may also be represented by, for example, average, by which the coarse adjustment compensation value may also be easily calculated.

After the coarse adjustment compensation value is calculated, all cell populations in the dot plot may be compensated using the coarse adjustment compensation value to update the dot plot.

It can be understood that, there can be fewer fine adjustment compensations by calculating the coarse adjustment compensation value. In other embodiments, the step of coarse adjustment compensation value calculation may alternatively be omitted to directly perform the fine adjustment compensation as described below.

In the fine adjustment compensation of the step S16, the progressive approximation algorithm used may be an iterative algorithm. The compensation value may be automatically calculated through the progressive approximation algorithm according to the position of the base cell population and all particles in the dot plot may be compensated using the compensation value. Then, the dot plot may be updated according to the compensation results. This step may specifically include:

setting the coarse adjustment compensation value as an initial compensation value or setting an initial compensation value, and setting an adjustment step length and an iteration termination condition; and compensating the plurality of cell populations in the dot plot and determining whether the compensated reference cell population meets the iteration termination condition. If not, the initial compensation value is automatically added or subtracted by the adjustment step length to obtain a current compensation value, and the plurality of cell populations in the dot plot may be continued to be compensated using the current compensation value until the iteration termination condition is met. The details will be described below with reference to FIG. 11.

The particles of all cell populations in the dot plot may be compensated by the compensation value using the following formula:

a resulting value of each particle in the compensated direction after the compensation=a current measurement value of each particle in the compensated direction−the compensation value*a current measurement value of each particle in the compensating direction.

The current measurement value of each particle in the compensating direction may remain unchanged.

Figure 11:
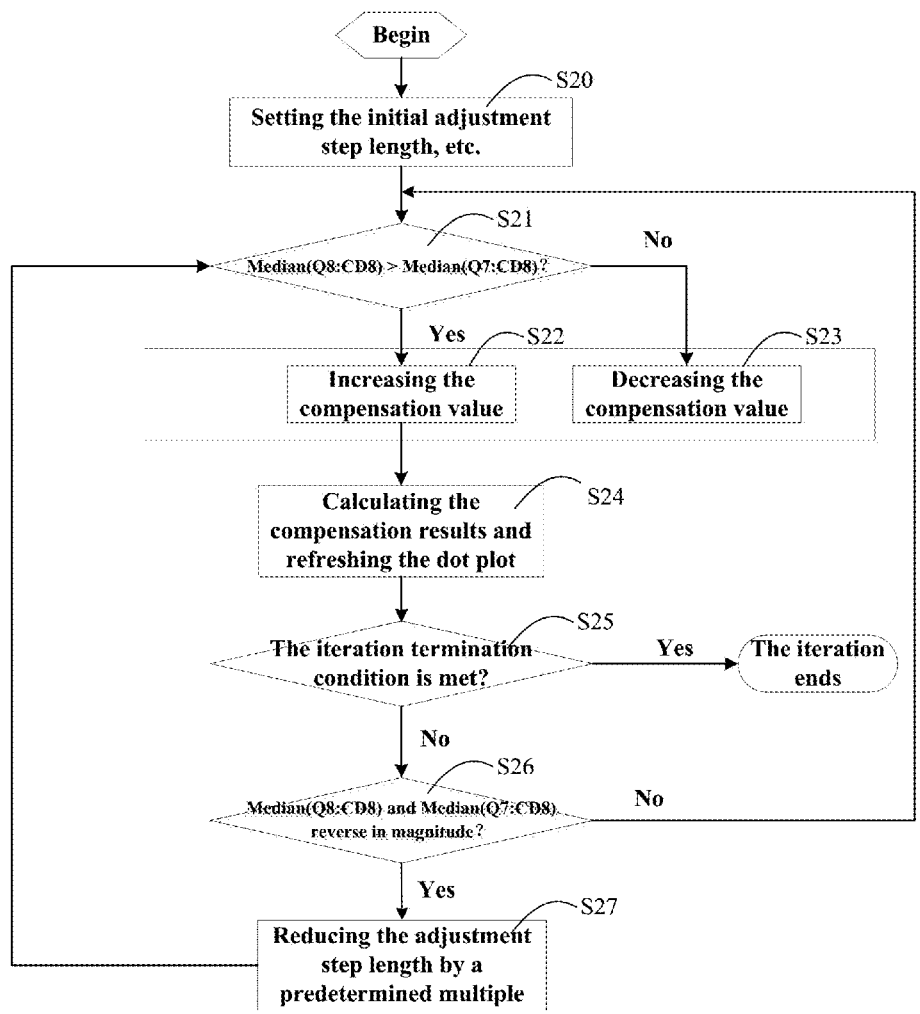
FIG. 11 is a flow chart for a fine adjustment compensation of an automatic compensation method provided by the present disclosure.

The specific processes of the fine adjustment compensation may be as shown in FIG. 11, which may include the following steps.

At step S20, the iteration termination condition, the initial adjustment step length and the initial compensation value may be set. The coarse adjustment compensation value obtained in the step S14 above may be set as the initial compensation value. In the case that there is no coarse adjustment compensation step, the initial compensation value may be directly set. In an embodiment, the initial adjustment step length may be set, for example, as 1%.

The iteration termination condition may be defined as follows:

an absolute value of a difference value between a median of the compensation resulting values of the particles of the base cell population in the compensated direction and a median of the compensation resulting values of the particles of the reference cell population in the compensated direction is less than a first predetermined value; or a ratio of an absolute value of a difference value between a median of the compensation resulting values of the particles of the base cell population in the compensated direction and a median of the compensation resulting values of the particles of the reference cell population in the compensated direction to the median of the compensation resulting values of the particles of the base cell population in the compensated direction or the median of the compensation resulting values of the particles of the reference cell population in the compensated direction is less than a second predetermined value; or an absolute value of a difference value between an average of the compensation resulting values of the particles of the base cell population in the compensated direction and an average of the compensation resulting values of the particles of the reference cell population in the compensated direction is less than a third predetermined value; or a ratio of an absolute value of a difference value between an average of the compensation resulting values of the particles of the base cell population in the compensated direction and an average of the compensation resulting values of the particles of the reference cell population in the compensated direction to the average of the compensation resulting values of the particles of the base cell population in the compensated direction or the average of the compensation resulting values of the particles of the reference cell population in the compensated direction is less than a fourth predetermined value.

The first, second, third and fourth predetermined values may be pre-determined as needed.

Specifically, in an embodiment, when taking the dot plot in FIG. 9 as an example, the iteration termination condition may be set as:

$$\frac{ABS(\text{Median}(Q8:CD8) - \text{Median}(Q7:CD8))}{MAX(ABS(\text{Median}(Q8:CD8)), ABS(\text{Median}(Q7:CD8)))} \leq 5\%$$

where Median(Q8:CD8) is the median of the measurement values of the particles of the reference cell population located in the region Q8 in the CD8 direction, Median(Q7:CD8) is the median of the measurement values of the particles of the base cell population located in the adjacent region Q7 in the CD8 direction, and the 5% is the second predetermined value as mentioned above.

At step S21, it may be determined whether the Median (Q8:CD8) is larger than the Median(Q7:CD8), and if yes, step S22 may be performed to increase the compensation value, i.e. the initial adjustment step length may be automatically added to the initial compensation value to obtain the current compensation value.

If not, step S23 may be performed to reduce the compensation value, i.e. the initial adjustment step length may be automatically subtracted from the initial compensation value to obtain the current compensation value.

At step S24, the particles of the plurality of cell populations in the dot plot may be compensated using the current compensation value, coordinates of the dot plot can be refreshed, and the current dot plot can be updated according to the compensation results.

At step S25, it may be determined whether the plurality of cell populations in the compensated dot plot meet the iteration termination condition. If yes, the fine adjustment compensation can be ended, and the current compensation value may be outputted as the final compensation value; if not, step S26 will be performed.

At step S26, it may be determined whether there is a reversion between the median/average of the measurement values of the particles of the base cell population in the compensated direction and the median/average of the measurement values of the particles of the reference cell population in the compensated direction. If yes, the adjustment step length may be reduced by a predetermined multiple and the iteration may then be continued. Specifically, in an embodiment, it may be determined whether the Median(Q8: CD8) and the Median(Q7:CD8) are reversed in their magnitudes. If not, the step S21 may be performed. The reversion herein may refer to that, for example, provided that there is always Median(Q8:CD8)>Median(Q7:CD8) during the iteration, the compensation value is continued to be adjusted for the iteration; when Median(Q7:CD8)>Median (Q8:CD8) arises for the first time, it is determined that there is the reversion between these two in their magnitudes. The reversion may mean that the Median(Q8:CD8) and the Median(Q7:CD8) are very close in their magnitudes, and in this case, the step S27 may then be performed.

At step S27, the initial adjustment step length may be reduced by a predetermined value (for example, reduced by a predetermined multiple; in an example, the initial adjustment step length may be reduced by 10 multiples to 0.1%) and the method may go back to the step S21 to repeat the iteration.

When the compensation results meet the iteration termination condition, the fine adjustment compensation can be ended and the current compensation value may be outputted as the final compensation value. In this way, the medians of the base cell population in the region Q7 and the reference cell population in the region Q8 can be closest to each other in the compensated direction (i.e. the CD8 direction). By finely adjusting the compensation value using the progressive approximation algorithm, the "smooth vertical and horizontal" distribution of the cell population particles in the dot plot can be achieved, i.e., the positions of the base cell population (i.e. the double-negative cell population) and the reference cell population can be substantially the same (within a predetermined range) in the compensated direction.

In other embodiments, it may also compare the averages of the base cell population in the region Q7 and the reference cell population in the region Q8 in the compensated direction (i.e. the CD8 direction) and make these two to be close to each other. In this way, the "smooth vertical and horizontal" distribution of the cell population particles in the dot plot may also be achieved, i.e., the positions of the base cell population (i.e. the double-negative cell population) and the reference cell population can be substantially the same (within a predetermined range) in the compensated direction.

It can be understood that the progressive approximation algorithm may also be, for example, a binary search algorithm in other embodiments.

It can be understood that, after the automatic calculation of the compensation value and the compensation to the particles in the dot plot, the user may also manually adjust the compensation value when he or she thinks that the compensation value automatically calculated is not suitable.

Figure 13:
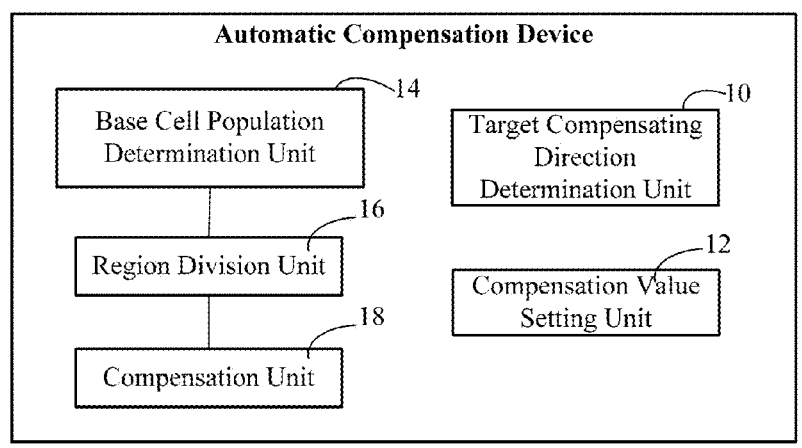
FIG. 13 schematically shows an embodiment of an automatic compensation device provided by the present disclosure.

As shown in FIG. 13, embodiments of the present disclosure also provide automatic compensation devices which may be used to analyze and process flow data generated by a flow cytometer. The device may include:

a target compensating direction determination unit 10 which may be used to, before the automatic compensation, determine at least one expected target compensating direction of a plurality of cell populations in a dot plot and display the target compensating direction in graph form for user's selection;

a compensation value setting unit 12 which may be used to manually adjust the compensation value and compensate the cell populations in all regions of the dot plot using the adjusted compensation value;

a base cell population determination unit 14 which may be used to determine a base cell population and a reference cell population in the plurality of cell populations according to positions of the plurality of cell populations in the dot plot which needs to be compensated, where the base cell population may be a double-negative cell population and the reference cell population may be a single-positive cell population in a compensating direction;

a region division unit 16 which may divide the dot plot into four regions according to a position of the base cell population such that the base cell population are located in a lower-left region and at least a portion of the reference cell population is located in a region which is in the compensating direction and adjacent to the base cell population. Specifically, the region division unit may divide the dot plot into four regions by generating a quadrant gate in the dot plot. The quadrant gate may be a regular quadrant gate which is formed by one straight line in a horizontal direction and one straight line in a vertical direction; or, the quadrant gate may be an irregular quadrant gate which is formed by at least one line in the horizontal direction and at least one line in the vertical direction.

a compensation unit 18 which may be used to automatically calculate the compensation value through a progressive approximation algorithm according to the position of the base cell population and to update the dot plot using the compensation value such that a position difference between the reference cell population and the base cell population in the dot plot in a compensated direction is within a predetermined range, where in the dot plot, the compensating direction is perpendicular to the compensated direction.

Figure 14:
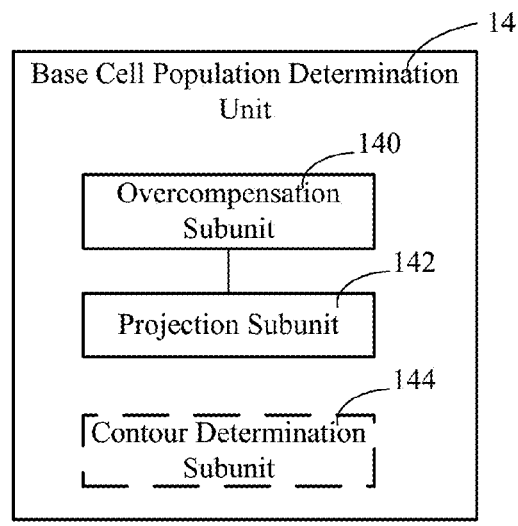
FIG. 14 schematically shows the base cell population determination unit in FIG. 13.

FIG. 14 schematically shows the base cell population determination unit 14 in FIG. 13.

The base cell population determination unit 14 may include:

an overcompensation subunit 140 which may be used to compensate the plurality of cell populations in the dot plot with a first compensation value, where the first compensation value is an overcompensation value; and a projection subunit 142 which may be used to project the plurality of cell populations onto the compensating direction and the compensated direction respectively to obtain histograms and determine one of the plurality of cell populations as the base cell population according to graphical peak features of the histograms.

In another embodiment, the base cell population determination unit 14 may further include:

a contour determination subunit 144 which may be used to acquire a cell population contour using an image algorithm at the lower-left region of the dot plot and determine the cell population corresponding to the cell population contour as the base cell population.

Figure 15:
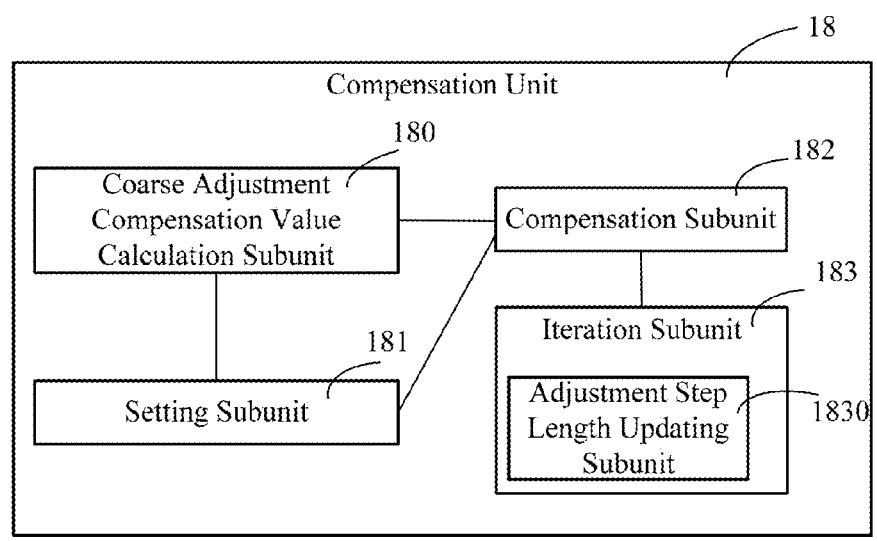
FIG. 15 schematically shows the compensation unit in FIG. 13.

FIG. 15 schematically shows the compensation unit 18 in FIG. 13.

The compensation unit 18 may further include:

a coarse adjustment compensation value calculation subunit 180 which may be used to calculate a coarse adjustment compensation value;

a setting subunit 181 which may be used to set the coarse adjustment compensation value as an initial compensation value or set an initial compensation value, and set an adjustment step length and an iteration termination condition;

a compensation subunit 182 which may be used to compensate the particles of all the plurality of cell populations in the dot plot with the compensation value set by the setting subunit; and an iteration subunit 183 which may compensate the plurality of cell populations in the dot plot and determine whether the compensated reference cell population meets the iteration termination condition; and if not, the iteration subunit may automatically add the adjustment step length to or subtract the adjustment step length from the initial compensation value to obtain a current compensation value, and continue to compensate the plurality of cell populations in the dot plot with the current compensation value, until the iteration termination condition is met. The specific details about the automatic addition or subtraction of the initial compensation value by the adjustment step length may be as described with respect to FIG. 11.

The coarse adjustment compensation value calculation subunit 180 may calculate the coarse adjustment compensation value with the following formula:

the coarse adjustment compensation value=(a measurement value of the reference cell population in the compensated direction−a measurement value of the base cell population in the compensated direction)/a measurement value of the reference cell population in the compensating direction.

The compensation subunit 182 may compensate the particles of all cell populations in the dot plot with the following formula:

a resulting value of each particle in the compensated direction after the compensation=a current measurement value of each particle in the compensated direction−the compensation value*a current measurement value of each particle in the compensating direction.

The compensation resulting value of each particle in the compensating direction may remain unchanged relative to its current measurement value in the compensating direction.

The iteration termination condition may be:

an absolute value of a difference value between a median of the compensation resulting values of the particles of the base cell population in the compensated direction and a median of the compensation resulting values of the particles of the reference cell population in the compensated direction is less than a first predetermined value; or a ratio of an absolute value of a difference value between a median of the compensation resulting values of the particles of the base cell population in the compensated direction and a median of the compensation resulting values of the particles of the reference cell population in the compensated direction to the median of the compensation resulting values of the particles of the base cell population in the compensated direction or the median of the compensation resulting values of the particles of the reference cell population in the compensated direction is less than a second predetermined value; or an absolute value of a difference value between an average of the compensation resulting values of the particles of the base cell population in the compensated direction and an average of the compensation resulting values of the particles of the reference cell population in the compensated direction is less than a third predetermined value; or a ratio of an absolute value of a difference value between an average of the compensation resulting values of the particles of the base cell population in the compensated direction and an average of the compensation resulting values of the particles of the reference cell population in the compensated direction to the average of the compensation resulting values of the particles of the base cell population in the compensated direction or the average of the compensation resulting values of the particles of the reference cell population in the compensated direction is less than a fourth predetermined value.

Further, the iteration subunit 183 may further include:

an adjustment step length updating subunit 1830 which may be used to determine whether there is a reversion between the median/average of the compensation resulting values of the particles of the base cell population in the compensated direction and the median/average of the compensation resulting values of the particles of the reference cell population in the compensated direction occurs; and if yes, the adjustment step length updating subunit may reduce the adjustment step length by a predetermined multiple and the iteration subunit may then continue the iteration.

It can be understood that, the progressive approximation algorithm may be a binary search algorithm in other embodiments.

More details may be as described above with respect to FIG. 6 to FIG. 12c and will not be described again.

Correspondingly, according to another aspect of the present disclosure, a flow cytometer is provided, which may include the automatic compensation device as described above. More details may be as described above with respect to FIG. 6 to FIG. 15 and will not be described again.

The advantages of the embodiments of the present disclosure may be as follows.

The automatic compensation method, device and corresponding flow cytometer provided by the embodiments of the present disclosure can automatically form the quadrant gate according to the features and the position information of the various cell populations in the dot plot, automatically perform the coarse adjustment compensation, and perform the fine adjustment compensation using the progressive approximation algorithm. Therefore, a suitable compensation value can be automatically calculated and the dot plot can be automatically updated, such that the plurality of cell populations are distributed in the compensated dot plot in a smooth horizontal and vertical form.

The embodiments of the present disclosure enable automatic compression using the graph-based adjustment. Therefore, user's workload is reduced and the accuracy is increased. Furthermore, since the compensation cell which needs to be compensated can be automatically set, the experience requirement for the user is greatly reduced.

A person ordinarily skilled in the art will understand that all or part of the processes of the methods in the embodiments above can be implemented through instructing related hardware by programs of a computer. The computer may include one or more general-purpose or special-purpose processors. The programs can be stored in a computer readable storage medium. When the programs are being executed, the processes as described in the embodiments above may be implemented. The storage medium may be disk, CD, ROM (Read-Only Memory) or RAM (Random Access Memory), etc.

The embodiments of the present disclosure have been described above. However, they do not intend to limit the scope of the present disclosure. The equivalents made according to the claims of the present disclosure still fall within the scope of the present disclosure.

The invention claimed is:

1. An automatic compensation method for analyzing and processing flow data, comprising:

determining a base cell population and a reference cell population in a plurality of cell populations according to positions of the plurality of cell populations in a dot plot which needs to be compensated, wherein the base cell population is a double-negative cell population and the reference cell population is a single-positive cell population adjacent to the base cell population in a compensating direction; and automatically calculating a compensation value through a progressive approximation algorithm according to a position of the base cell population and compensating particles of the plurality of cell populations in the dot plot with the compensation value, such that a position difference between the reference cell population and the base cell population in a compensated direction in the compensated dot plot is within a predetermined range.

2. The automatic compensation method of claim 1, wherein determining the base cell population in the plurality of cell populations according to the positions of the plurality of cell populations in the dot plot which needs to be compensated comprises:

compensating the plurality of cell populations in the dot plot with a first compensation value, wherein the first compensation value is an overcompensation value; and projecting the plurality of cell populations onto the compensating direction and the compensated direction respectively to obtain histograms and determining one of the plurality of cell populations as the base cell population according to graphical peak features of the histograms;

or, acquiring a cell population contour using an image algorithm at a lower-left region of the dot plot and determining a cell population corresponding to the cell population contour as the base cell population.

3. The automatic compensation method of claim 2, further comprising, after determining the base cell population and the reference cell population in the plurality of cell populations, dividing the dot plot into four regions according to the position of the base cell population such that the base cell population is located in a lower-left region.

4. The automatic compensation method of claim 3, wherein dividing the dot plot into four regions according to the position of the base cell population comprises:

dividing the dot plot into the four regions by generating a quadrant gate in the dot plot, wherein the quadrant gate is a regular quadrant gate which is formed by one straight line in a horizontal direction and one straight line in a vertical direction, or an irregular quadrant gate which is formed by at least one line in a horizontal direction and at least one line in a vertical direction.

5. The automatic compensation method of claim 4, further comprising:
before the automatic compensation, determining at least one expected target compensating direction of the plurality of cell populations in the dot plot and displaying the target compensating direction in graph form for user's selection;
or,
before or after the automatic compensation, manually adjusting the compensation value and compensating the plurality of cell populations in the dot plot with the adjusted compensation value.

6. The automatic compensation method of claim 1, wherein automatically calculating the compensation value through the progressive approximation algorithm according to the position of the base cell population and compensating the particles of the plurality of cell populations in the dot plot with the compensation value comprises:
compensating the particles of the plurality of cell populations in the dot plot with the compensation value using the following formula:

a compensation resulting value of each particle in the compensated direction=a current measurement value of each particle in the compensated direction−the compensation value*a current measurement value of each particle in the compensating direction;

wherein a compensation resulting value of each particle in the compensating direction remains unchanged relative to the current measurement value of each particle in the compensating direction.

7. The automatic compensation method of claim 6, further comprising calculating a coarse adjustment compensation value and compensating the dot plot with the coarse adjustment compensation value,
wherein the coarse adjustment compensation value is calculated using the following formula:

the coarse adjustment compensation value=(a measurement value of the reference cell population in the compensated direction−a measurement value of the base cell population in the compensated direction)/a measurement value of the reference cell population in the compensating direction.

8. The automatic compensation method of claim 7, wherein the progressive approximation algorithm is an iterative algorithm, and automatically calculating the compensation value through the progressive approximation algorithm according to the position of the base cell population and compensating the particles of the plurality of cell populations in the dot plot with the compensation value comprises:
setting an initial compensation value, an adjustment step length and an iteration termination condition, wherein the initial compensation value is the coarse adjustment compensation value or a preset compensation value; and
compensating the particles of the plurality of cell populations in the dot plot and determining whether the compensated reference cell population meets the iteration termination condition; if no, automatically adding or subtracting the initial compensation value by the adjustment step length to obtain a current compensation value, and continuing to compensate the particles of the plurality of cell populations in the dot plot with the current compensation value, until the iteration termination condition is met.

9. The automatic compensation method of claim 8, wherein the iteration termination condition is:
an absolute value of a difference value between a median of the compensation resulting values of the base cell population in the compensated direction and a median of the compensation resulting values of the reference cell population in the compensated direction is less than a first predetermined value; or
a ratio of an absolute value of a difference value between a median of the compensation resulting values of the base cell population in the compensated direction and a median of the compensation resulting values of the reference cell population in the compensated direction to the median of the compensation resulting values of the base cell population in the compensated direction or the median of the compensation resulting values of the reference cell population in the compensated direction is less than a second predetermined value; or
an absolute value of a difference value between an average of the compensation resulting values of the base cell population in the compensated direction and an average of the compensation resulting values of the reference cell population in the compensated direction is less than a third predetermined value; or
a ratio of an absolute value of a difference value between an average of the compensation resulting values of the base cell population in the compensated direction and an average of the compensation resulting values of the reference cell population in the compensated direction to the average of the compensation resulting values of the base cell population in the compensated direction or the average of the compensation resulting values of the reference cell population in the compensated direction is less than a fourth predetermined value.

10. The automatic compensation method of claim 9, wherein automatically adding or subtracting the initial compensation value by the adjustment step length to obtain the current compensation value and continuing to compensate the particles of the plurality of cell populations in the dot plot until the iteration termination condition is met further comprises:
determining whether there is a reversion in magnitude between the median/average of the compensation resulting values of the base cell population in the compensated direction and the median/average of the compensation resulting values of the reference cell population in the compensated direction; if yes, reducing the adjustment step length by a predetermined value and continuing the iteration.

11. An automatic compensation device for analyzing and processing flow data, comprising one or more processors that are configured to:
determine a base cell population and a reference cell population in a plurality of cell populations according to positions of the plurality of cell populations in a dot plot which needs to be compensated, wherein the base cell population is a double-negative cell population and the reference cell population is a single-positive cell population adjacent to the base cell population in a compensating direction; and
automatically calculate a compensation value through a progressive approximation algorithm according to a position of the base cell population and update the dot plot using the compensation value such that a position difference between the reference cell population and the base cell population in the dot plot in a compensated direction is within a predetermined range.

12. The automatic compensation device of claim 11, wherein the one or more processors are further configured to:
   compensate the plurality of cell populations in the dot plot with a first compensation value, wherein the first compensation value is an overcompensation value; and
   a projection subunit which is used to project the plurality of cell populations onto the compensating direction and the compensated direction respectively to obtain histograms and determine one of the plurality of cell populations as the base cell population according to graphical peak features of the histograms.

13. The automatic compensation device of claim 12, wherein the one or more processors are further configured to:
   divide the dot plot into four regions according to the position of the base cell population such that the base cell population is located in a lower-left region.

14. The automatic compensation device of claim 11, wherein the one or more processors are further configured to:
   compensate particles of the plurality of cell populations in the dot plot with the compensation value using the following formula:

a compensation resulting value of each particle in the compensated direction=a current measurement value of each particle in the compensated direction−the compensation value*a current measurement value of each particle in the compensating direction;

wherein a compensation resulting value of each particle in the compensating direction remains unchanged relative to the current measurement value of each particle in the compensating direction.

15. The automatic compensation device of claim 14, wherein the one or more processors are further configured to calculate a coarse adjustment compensation value with the following formula:

the coarse adjustment compensation value=(a measurement value of the reference cell population in the compensated direction−a measurement value of the base cell population in the compensated direction)/a measurement value of the reference cell population in the compensating direction.

16. The automatic compensation device of claim 15, wherein the progressive approximation algorithm is an iteration algorithm, and the one or more processors are further configured to:
   set an initial compensation value, an adjustment step length and an iteration termination condition; and
   compensate the particles of the plurality of cell populations in the dot plot and determine whether the compensated reference cell population meets the iteration termination condition; and if no, automatically add the adjustment step length to or subtract the adjustment step length from the initial compensation value to obtain a current compensation value, and continue to compensate the particles of the plurality of cell populations in the dot plot with the current compensation value, until the iteration termination condition is met.

17. The automatic compensation device of claim 16, wherein the iteration termination condition is:
   an absolute value of a difference value between a median of the compensation resulting values of the base cell population in the compensated direction and a median of the compensation resulting values of the reference cell population in the compensated direction is less than a first predetermined value; or
   a ratio of an absolute value of a difference value between a median of the compensation resulting values of the base cell population in the compensated direction and a median of the compensation resulting values of the reference cell population in the compensated direction to the median of the compensation resulting values of the base cell population in the compensated direction or the median of the compensation resulting values of the reference cell population in the compensated direction is less than a second predetermined value; or
   an absolute value of a difference value between an average of the compensation resulting values of the base cell population in the compensated direction and an average of the compensation resulting values of the reference cell population in the compensated direction is less than a third predetermined value; or
   a ratio of an absolute value of a difference value between an average of the compensation resulting values of the base cell population in the compensated direction and an average of the compensation resulting values of the reference cell population in the compensated direction to the average of the compensation resulting values of the base cell population in the compensated direction or the average of the compensation resulting values of the reference cell population in the compensated direction is less than a fourth predetermined value.

18. The automatic compensation device of claim 17, wherein the one or more processors are further configured to:
   determine whether there is a reversion in magnitude between the median/average of the compensation resulting values of the base cell population in the compensated direction and the median/average of the compensation resulting values of the reference cell population in the compensated direction; and if yes, the adjustment step length updating subunit reduces the adjustment step length by a predetermined value and the iteration subunit then continuous the iteration.

19. The automatic compensation device of claim 11, wherein the one or more processors are further configured to:
   before the automatic compensation, determine at least one expected target compensating direction of the plurality of cell populations in the dot plot and display the target compensating direction in graph form for user's selection.

20. The automatic compensation device of claim 11, wherein further comprising an interaction interface for receiving user input; the user input is used for adjusting the compensation value, and the one or more processors are further configured to compensate the plurality of cell populations in the dot plot using the adjusted compensation value.

* * * * *